United States Patent [19]

Haseltine et al.

[11] Patent Number: 4,738,922
[45] Date of Patent: Apr. 19, 1988

[54] TRANS-ACTING TRANSCRIPTIONAL FACTORS

[75] Inventors: William A. Haseltine; Joseph G. Sodrowski, both of Cambridge; Craig A. Rosen, Brookline, all of Mass.

[73] Assignee: Dana Farber Cancer Institute, Boston, Mass.

[21] Appl. No.: 614,297

[22] Filed: May 25, 1984

[51] Int. Cl.$^4$ .................. C12N 15/00; C12N 7/00; C12N 1/00

[52] U.S. Cl. .................. 435/68; 435/235; 435/172.3; 435/91; 435/320; 935/39; 935/34; 935/32; 536/27

[58] Field of Search ............... 536/27; 435/172.3, 317, 435/68; 935/32, 36

[56] References Cited

U.S. PATENT DOCUMENTS 4,405,712 9/1983 Vande Woude et al. ........ 435/172.3

OTHER PUBLICATIONS

Green, M. et al., Nov. 1983, Cell 35:137–148.
Smith, G. et al., Dec. 1983, MCB 3:2156–2165.
Broome, S., 1982, In Eukaryotic Viral Vectors, pp. 139–144, (ed), Y. Gluzman, Cold Spring Harbor Laboratory, N.Y.
Laimins, L. et al., 1982, PNAS 79:6453–6457.
Shimotohno, K. et al., Feb. 1984, PNAS 81:1079–1083.
Chen, I. et al., 17 May 1984, Nature 309:276–279.

Primary Examiner—Thomas G. Wiseman
Assistant Examiner—S. Seidman
Attorney, Agent, or Firm—David G. Conlin; Ernest V. Linek; Ronald I. Eisenstein

[57] ABSTRACT

This invention describes the discovery of a novel phenomena in retrovirus transcription, namely transcriptional trans-activation. Described herein are novel trans-acting factors which may be employed to enhance the production of heterologous genes. Described is a novel trans-acting directing gene, designated herein as the "luk" gene and the 35,000 to 45,000, more specifically about 42,000 dalton molecular weight protein encoded thereby.

The present invention demonstrates the LTR elements of HTLV can function as transcriptional promoters for heterologous genes on both unintegrated and integrated DNA. In general, the HTLV-1 LTR is a stronger promoter than is the HLTV-II LTR in its requirements for cellular and/or viral trans-acting factors in order to function efficiently. HTLV infection results in the production of trans-acting factors that dramatically increase the rate of HTLV LTR-promoted transcription.

26 Claims, 3 Drawing Sheets

TRANS-ACTING TRANSCRIPTIONAL FACTORS

FIELD OF THE INVENTION

The present invention demonstrates that LTR elements of HTLV can function as transcriptional promoters for heterologous genes on both unintegrated and integrated DNA. In general, the HTLV-I LTR is a stronger promoter than is the HLTV-II LTR in its requirements for cellular and/or viral trans-acting fractors in order to function efficiently. HTLV infection results in the production of trans-acting factors that dramatically increase the rate of HTLV LTR-promoted transcription.

BACKGROUND OF THE INVENTION

Human T cell leukemia viruses (HTLV) comprise a family of exogenous human retroviruses. HTLV subtypes are characterized by differences in immunocompetition reactions of viral core proteins, and in nucleic acid hybridization heteroduplex maps, restriction enzyme analysis and DNA sequence analysis. HTLV-I is the etiologic agent of clinically aggressive adult T cell leukemia/lymphoma (ATLL), a disease characterized by an aggressive clinical course with a poor prognosis. By contrast, HTLV-II is an infrequent HTLV isolate orginally derived from a patient with a clinically benign T cell variant of hairy cell leukemia. Recently, a new group of HTLV viruses, HTLV III, have been isolated from patients with the acquired immune deficiency syndrome (AIDS). Although both HTLV-I and HTLV-II are associated with malignancies involving the mature OKT4+ subset of T lymphocytes, the clinical course and outcome of these malignancies differ markedly.

The full spectrum of diseases associated with HTLV is not known, and prior to this invention, the conventional widom has held that the factors which govern whether an HTLV will cause neoplasia, an immunodifficiency, or both, have not been defined. (Mitsuya, 1984).

The present invention describes a specific region of the HTLV genomes which governs the promotional strength, and host cell range for each virus. Also discussed is novel genomic factor, luk, which controls the tissue specificity for the various HTLV.

SUMMARY OF THE INVENTION

This invention describes the discovery of a novel phenomena in retrovirus transcription, namely trans-activation. Described herein are novel trans-acting factors which may be employed to enhance the production of heterologous genes. Described is a novel trans-acting directing gene, designated herein as the "luk" gene and the 35,000 to 45,000, more specifically about 42,000 dalton molecular weight protein encoded thereby.

DETAILED DESCRIPTION

Figure 1:
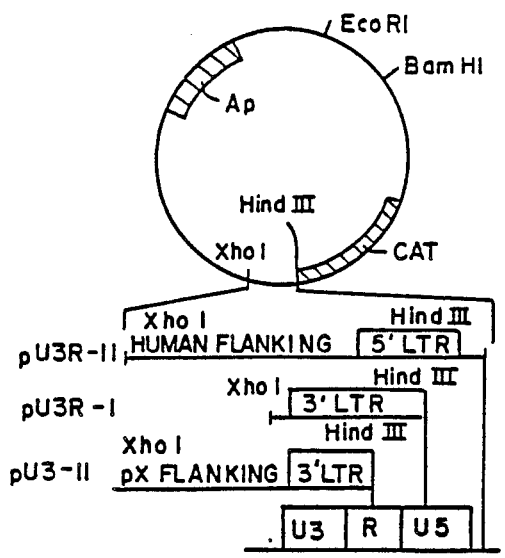
FIG. 1 depicts schematic representations and constructions of recombinant plasmids utilized in Example 1. The diagram depicts the region of the HTLV LTR's placed 5' to the CAT gene.

LTR regions of HTLV I and II diverge markedly in sequences (Shimotohmo, 1984). It is herein reported that the long terminal repeat elements of HTLV I and II can, in the appropriate environment, promote the expression of heterologous genes. It has been discovered that species specific and tissue specific differences occur in the rate of CAT gene expression under control of the HTLV LTRs. It has also been discovered that there are major differences in the activity of the HTLV I and II transcriptional elements. The most striking set of observations indicate that in cells infected in HTLV trans-acting factors markedly stimulate transcription by the HTLV LTR. The trans-acting transcriptional factors display some type specificity for activation of HTLV I and II transcriptional elements. Discussed herein are potential mechanisms whereby these differences in LTR transcriptional activity and trans-activation might lead to different clinical consequences following infection by HTLV subtypes.

The sequence of the 3' terminus of the human T lymphotropic virus Type II (HTLV-II) was determined and compared to the 3' termini of the genomes of HTLV-I, bovine leukemia virus, and mouse mammary tumor viruses. All of these viruses contain long open reading frames sufficient to encode proteins in the molecular weight region of 38-40,000.

The nucleotide sequence of 1,557 bases of the 3' terminal region of the HTLV II can be divided into two domains. One domain, 547 nucleotides long, is located at the 5' end of the sequence and has either no or very little sequence similarity to the corresponding regions in HTLV-I. This domain is herein called the non-conserved region (NCR). A second region, 1,011 nucleotides long, comprises the 3' portion of this region. This sequence is very similar to that of HTLV-I. The sequence can be aligned with that of HTLV-I and is identical at 716 of 1,011 nucleotides (70%) homology.

The perimeters of the 1,011 nucleotide long sequence of the HTLV-II genome correspond precisely with a single long open reading frame capable of encoding a polypeptide 337 amino acids long. A corresponding sequence of HTLV-I also encompasses a single long open reading frame capable of encoding a polypeptide 359 amino acids long.

Proteins encoded by HTLV-I and II are of approximately the same length and are identical in 278 of 337 of the amino acids (82% identity). The degree of similarity of these two proteins is even more striking if conservative amino acid substitutions are considered (95% similar). The distribution of hydrophylic and hydrophobic regions of these proteins is remarkably similar.

Several other long open reading frames exist in the LTR regions of both Type I and Type II HTLV. None of these are found to be common to both HTLV-I and HTLV-II. No regions of predicted protein sequence similarity could be found upon comparison of the coding capacity of the HTLV-I and II viruses in the 3' region in any reading frame with the notable exception of the 3' terminal sequence discussed above. In particular the pX1, X2 and X3 long open reading frames noted by Seiki, (1983) have no counterpart within the 3' sequence of HTLV-II, whereas the pX4 corresponds to the carboxyl terminus of the long open reading frame noted above. An 11 base pair deletion in the NCR region of HTLV-C relative to that of HTLV-I, apparently has no effect on the biological activity of the virus.

The 3' terminal region of HTLV contains a newly discovered gene that encodes a protein that is at least molecular weight 38,000. A protein of molecular weight 40-42,000 in HTLV-I-infected cell lines has been noted that is recognized by sera of persons infected with HTLV-I, but not by control human sera.

The 3' genomes of the two other retroviruses, bovine leukemia virus (BLV) and murine mammary tumor virus (MMTV) also contain long open reading frames located 3' to the envelope glycoprotein gene that could encode proteins of a size similar to that of the HTLV virus.

Like HTLV, the BLV contains a long sequence located between the 3' end of the envelope glycoprotein and the 3' band of the U3 region. The 3' domain of this sequence contains an open reading frame 987 nucleotides long that could encode a polypeptide of 328 amino acids. As is the case for HTLV, a consensus splice acceptor site is located at the 5' end of the long open reading frame. BLV infected cells contain a small mRNA species that includes these 3' sequences.

In many respects diseases induced by BLV resemble those induced by HTLV-I. The diseases have a long latent period that is sometimes preceded by lymphocytosis (Ferrer et al., 1974; Gallo & Wong-Staal, 1982). In both diseases there is no chronic viremia in the target organs preceding the disease and there is no preferred site of DNA integration of the provirus in the tumor cells (Paul et al., 1977; Kettman et al., 1983; Gregoire et al., 1984; Gallo & Wong-Staal, 1982; Hahn et al., 1983). Thus, the genome of BLV contains a luk region similar to that postulated for the HTLV viruses that mediates a transforming effect of viral infection.

The presence of a long open reading frame at the 3' terminus of the viral genome is reminiscent of the structure of murine mammary tumor viruses. These viruses contain a long open reading frame located between the 3' end of the env gene and the transcription initiation signals (Kennedy et al., 1982; Donehower et al., 1983).

Regions of significant similarity observed for the proteins of HTLV and BLV are also present in co-linear positions in the MMTV polypeptide. Optimal alignment of the conserved domains of the MMTV polypeptide with respect to HTLV is achieved by postulating precisely the same deletions as were required to obtain optimal alignment of the BLV and HTLV proteins. The MMTV possesses identical or conserved amino acids in 95 of 320 (18%) positions with respect to HTLV-I and 85 to 320 (25%) as compared to BLV. The distribution of hydrophobic and hydrophylic domains is remarkably similar for all of these proteins.

Experience with murine leukemia viruses indicates that the retroviral long terminal repeat (LTR) is the major determinant of the tissue tropism (C. Rosen and W. Haseltine, manuscript in preparation), and specific disease introduced by these viruses (Lenz, 1983; Hopkins, 1983; Desgrosillers, 1983). Rearrangements of the repetitive elements of the LTR U3 region distinguish animal leukemia viruses such that they differ in the tissue which they infect and/or in the disease they cause. These rearrangements affect the ability of the LTR to function as a transcriptional promoter/enhancer element in specific cell types.

Construction of HTLV-CAT Recombinant Plasmids

The transcriptional control elements of animal retroviral LTRs are contained within the U3 regin. Since the usually long R region of the HTLV LTR might play a role in transcriptional regulation, the entire U3 and R regions of HTLV I were inserted 5' to the chloramphenicol acetyltransferase (CAT) gene (Gorman, 1982) (pU3R-I and pU3R-II) (See FIG. 1). A third plasmid that contained only the U3 and a portion of the R region of HTLV II was also constructed, pU3-II (FIG. 1). The activity of the CAT gene in transient transfection assays was compared to the activity of other plasmids that contained either the entire SV40 enhancer-promoter region (pSV2CAT), the promoter of SV40 without the 72 base repeat regions that comprise the SV40 enhancer (pSVIX CAT), or the entire LTR of Rous sarcoma virus (Gorman, Merlino, 1982) (pRSVCAT) located 5' to the CAT gene.

To test the transcriptional activity of the inserted HTLV sequences, the plasmid DNA was introduced into cells via transfection using either the calcium phosphate (Graham, 1973) or the DEAE dextran methods (Queen, 1983). Various cell lines differ in their ability to take up and express transfected DNA. In each experiment the CAT activity directed by the plasmids that contained HTLV sequences was normalized to that of plasmids that contained the SV40 enhancer promoter elements. The SV40 transcriptional elements have been shown to function in a wide variety of cell types and have been utilized as relatively neutral reference promoters in similar studies (Gorman, Merlino, 1982; Walker, 1983.

Expression of the CAT Gene in Fibroblast and Epithelial Cell Lines

The ability of the LTR sequences of HTLV I and II to act as transcriptional elements in fibroblast and epithelioid cells of mouse, simian, and human origin was tested as described below.

Figure 2:
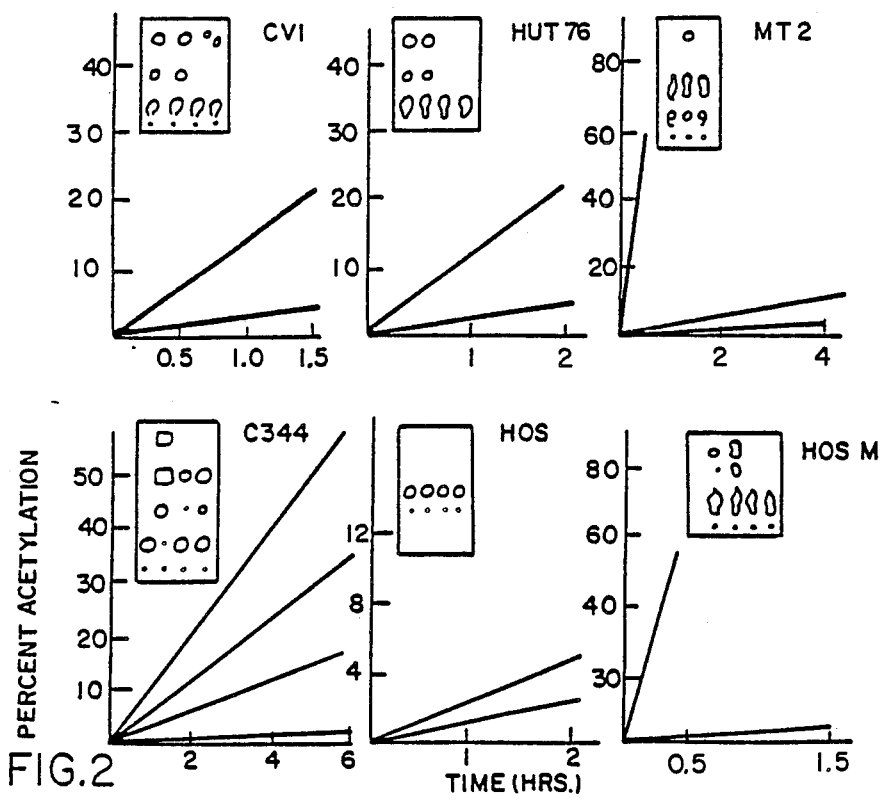
FIG. 2 illustrates the transient expression of the CAT gene directed by the HTLV LTR transcriptional elements. The graphs depict typical CAT assays over the time course indicated. All experiments were performed a minimum of 3 times with results differing by no more than 30 percent. Symbols represent CAT activity directed by the plasmids, pVSR-I (○), pSV2CAT (●), pV3-II (□), pV3R-II (■), and pSVXCAT (Δ). Insets show actual autoradiograms of a CAT Assay and represent conversions obtained from one time period within the linear range of the assay.
Figure 3:
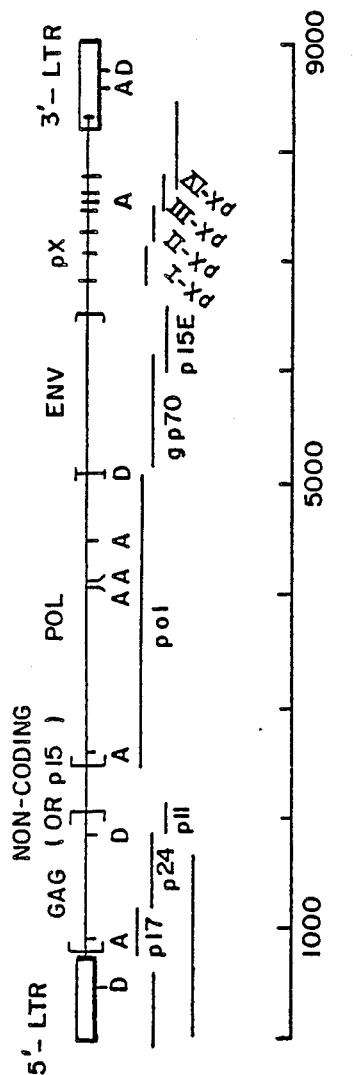
FIG. 3 is a schematic representation of the HTLV viral DNA showing the relative location of the gag, pol and env genes, as well as the PX or lux gene. The luk gene results in production of trans-acting factors and encodes a 35,000 to 45,000 molecular weight protein.

The data of Table 1 and FIG. 2 show that in murine fibroblasts (NIH 3T3), the activity of plasmids that contain the LTR sequences of HTLV I was comparable to that of pSV2CAT and much higher than the level of the plasmid that contains the SV40 promoter sequence alone. The level of CAT activity in cells transfected with pRSV CAT was highest in this cell line. The HTLV I sequences also yielded appreciable levels of CAT activity upon transfection into simian (CV-1) cells, although it was lower than that observed for the pSV2CAT plasmid. The LTR sequences of HTLV II directed very low levels of CAT activity in both of these murine and simian cells lines. These experiments demonstrate that the LTR sequences of HTLV I can function as efficient transcriptional elements in cells of different species, and that they exhibit markedly enhanced proportional strength in these cell types as compared to the HTLV II LTR sequences.

TABLE 1

Relative CAT Activity[a]

| Cell line | Description | pSV2CAT | pU3R-I | pU3-II | pU3R-II | RSVCAT |
|---|---|---|---|---|---|---|
| CV1 | Simian, fibroblast cell line | 1.0 | 0.2 | [b] | [b] | ND |
| NIH3T3 | Murine fibroblast cell line | 1.0 | 0.92 | [b] | [b] | ND |
| M1 | SV40 transformed cell line | 1.0 | 2.2 | [b] | [b] | ND |
| Hela | Human cervical carcinoma line | 1.0 | 2.16 | [b] | [b] | 1.6 |
| NC37 | EBV immortalized human B lymphocyte line | 1.0 | 4.5 | [b] | [b] | ND |
| HUT78 | Transformed human lymphocyte line | 1.0 | 4.5 | [b] | [b] | 2.1 |
| C8166 | HTLV-I infected non-producer | 1.0 | 74 | [b] | [b] | ND |
| HUT102 | HTLV-I producer T lymphocyte line | 1.0 | 28 | 1.4 | 1.7 | ND |
| MT2 | HTLV-I producer T lymphocyte line | 1.0 | 180 | ND | 5.5 | 2.4 |
| C344 | HTLV-II producer | 1.0 | 140 | 40 | 95 | ND |
| HOS | Human osteocarcinoma cell line | 1.0 | 0.7 | [b] | [b] | ND |
| HOS/M | HTLV-I infected | 1.0 | 75 | [b] | [b] | 1.0 |

[a]The values shown represent a kinetic analysis of CAT activity directed by the individual plasmids relative to pSV2CAT.
[b]CAT activity was too low to quantitate.
ND - No Data The level of CAT activity upon transfection of the plasmids that contain the HTLV I LTR sequence into human fibroblast and epithelioid cells, HeLa, and M1 was greater than that observed upon transfection of the same cells with the pSV2CAT containing plasmid. Negligible CAT activity was observed upon transfection of these cells with plasmids that contained HTLV Type II sequences. Thus, HTLV I LTR sequences can function as transcriptional control elements in human cells that are not the natural targets for HTLV infection, whereas the HTLV II LTR sequences cannot.

LTR-mediated retroviral gene expression in infected cells occurs from a provirus stably integrated into the host cell genome, whereas in a transient assay the transfected DNA directing transcription exists primarily in an extrachromosomal state. To determine if the results obtained from transient assays were relevant to an understanding of HTLV LTR function in the integrated provirus, the HTLV LTR sequences used to direct CAT expression were positioned upstream of the neomycin phosphotransferase gene (Southern, 1982). These plasmids were transfected into murine and human cell lines (Table II) and stably transfected colonies were selected in the presence of a neomycin analog G-418. The number of G-418 resistant colonies obtained relative to that of the SV40-promoted neomycin phosphotransferase gene demonstrated a close parallel to the transient expression data. The levels of CAT activity in transient assays provided reasonable insight into the ability of the transcriptional element being tested to function upon integration into the host chromosome.

TABLE 2

| Cell line | pU3R-I | pU3-II | PSV2NEO | RSVNEO |
|---|---|---|---|---|
| NIH 3T3 | 24 | 0 | 24 | 82 |
| HeLa | 15 | 0 | 7 | 97 |

The recombinant plasmids indicated above were constructed by cleavage of the HTLV-CAT recombinants with Hind III-Bam HI and replacing the CAT coding sequence with the gene coding neomycin resistance. Twenty four hours prior to transfection 1 × 106 cells were seeded into 100 cm2 dishes. Transfection was done using the calcium phosphate DNA coprecipitation method using 3 ug of CsCl banded DNA. After 48 hours cells were replated onto 150 cm2 dishes and selected in medium containing G-418 (400 ug/ml). Colonies were counted 2-3 weeks after transfection.

Expression in Human Lymphoid Cells

In naturally acquired HTLV infection, the majority of infected cells are of the T cell lineage. However, some HTLV producing cells expressing B cell markers have been isolated. To determine the relative promotional strength of the LTR sequences within lymphocytes, cell lines of lymphoid origin were transfected with the plasmids described above. The cell lines used were: HUT78, an OKT4+ human T cell line derived from an HTLV-negative patient who with Sezary syndrome (this cell line lacks HTLV proviral sequences); NC37, an Epstein-Barr virus—immortalized B cell line established from a normal donor; and L691; a murine lymphoid cell line that expresses T cell markers.

The LTR sequences of HTLV I directed the synthesis of appreciable levels of the CAT gene product in both the human T and B cells (FIG. 2, Table 1). The ratio of pU3RI-CAT to that of pSV2CAT activity was approximately twice as high as this ratio in fibroblasts and epithelioid cell lines. Higher CAT activity relative to the level induced by pSV2CAT was observed in the murine cell line transfected with the plasmid pU3R-I. These findings demonstrate that both species-specific and cell type-specific factors modulate the activity of the Surprisingly, transfection of the HUT78 or NC37 cells with plasmids that contained HTLV II LTR sequences resulted in no appreciable level of CAT activity. This suggested that a human lymphoid environment is not sufficient for the efficient function of the HTLV II LTR and that substantial differences in the requirements for the LTR function of HTLV I and HTLV II exist.

Expression in HTLV Infected Cells

The inactivity of the HTLV II LTR in the lymphoid cell lines suggested that factors specific to the HTLV target cell might be required for efficient expression of the CAT gene under control of the HTLV LTRs. For this reason HTLV-producing cell lines derived from infected individuals, or cell lines established by co-cultivation of human primary lymphocytes were transfected with HTLV producer cell lines. The cell lines used included: HUT102, an HTLV I producing OKT4+ cell line established from a patient with an HTLV associated adult T cell leukemia/lymphoma (mycosis fungocides); MT2, an HTLV I producing OKT4+ cell line established by immortalization of primary T lymphocytes after cocultivation with an HTLV producer cell line; C3-44, an immortalized HTLV II producing cell line derived by cocultivation of primary lymphocytes with patient cells; and C81-66, an HTLV I immortalized OKT4+ primary T cell that does not produce virus.

The results obtained upon transfection of these cell lines with the plasmid that contains the HTLV I LTR sequences were remarkable and unexpected. The level of CAT activity was dramatically increased relative to that of pSV2CAT, rating from 25 to 180-fold greater.

Contributing to this large relative ratio of Type I LTR CAT activity is a consistent decrease in the activity of the pSV2CAT and RSVCAT plasmids in these cells. This may be due to a decreased efficiency in the uptake and expression of transfected DNA by these cells, or to specific or non-specific factors down-regulating the promotional activity of these elements. Normalizing for DNA uptake indicates that the increased level of CAT activity directed by the pU3-RI plasmid in infected cells represents a real and not solely a relative increase compared to levels in uninfected cells. Since the extrachromosomal state of transiently expressing DNA precludes efficient cis-activation, these results suggest that trans-acting factors in HTLV-infected cells stimulate the transcriptional ability of the HTLV LTR. Although low, the CAT activity directed by the plasmids containing HTLV-II LTR sequences is substantially higher in most of the cells that contain HTLV-I proviruses than it is in unifected cells.

To determine if the HTLV II LTR sequences could function in a cell line producing Type II virus, the same plasmids were used to transfect the C3-44 cell line. In this cell line, a very high level of CAT activity was observed for both the pU3R-II and pU3-II plasmids. The level of CAT activity is approximately forty times that of the same cells transfected with pSV2CAT DNA. This demonstrates that in the proper cellular environment, the HTLV-II LTR also functions as an efficient transcriptional element.

The CAT activity of the plasmid containing HTLV I LTR sequences was also very high in C3-44 cells, approximately 135 times that of pSV2CAT. Thus, even in the target cell for HTLV-II infection, the HTLV-I LTR exhibits greater promotional strength than does the HTLV-II LTR.

T lymphocytes infected with HTLV exhibit changes that also characterize T cells activated by exposure to mitogenic or antigenic stimuli (Popovic, 1983).

To examine whether T cell activation alone might modify the cellular environment to allow increased transcriptional activity of the HTLV LTRs, the HTLV-CAT and control plasmids were transfected into an immature human T cell line, Jurkat, both in the presence and absence of the T cell mitogen phytohemaglutinin (PHA). No effect of PHA stimulation on the relative levels of CAT activity was seen directed by any of the plasmids. It was concluded that PHA activation of T cells alone was insufficient to account for the stimulation of CAT activity seen in infected cells transfected with the HTLV-CAT plasmids.

Test for Transcting Transcriptional Factors

To directly test whether the high degree of HTLV LTR function in HTLV-infected T lymphocyte subsets viral-encoded or -induced factors play a role in this phenomenon, the plasmids were introduced into HOS/M cells, a cell line established by infecting a human osteosarcoma line (HOS) in vitro with HTLV-I. Although HOS/M cells produce HTLV-I virions and express viral proteins, they do not express receptors for T cell growth factor, OKT antigens, new HLA antigens or lymphokines; properties that characterize HTLV-infected lymphoctyes. Thus, although viral proteins are produced, the HOS/M cellular environment differs markedly from HTLV-infected tumor cells and should help distinguish between the above alternatives. As noted above, the HTLV-I LTR functioned in the uninfected HOS cells somewhat less efficiently than the SV40 early promoter. By contrast, PU3R-I directed CAT expression was fifty-fold higher than that of pSV2CAT in HOS/M cells. Moreover, consistent with our results in HTLV-I-infected lymphocytes, PURR-II and PU3R-II do not express significant levels of CAT in the transfected HOS/M cells.

The phenomenon of transcriptional trans-activation is novel for retroviruses. HTLV trans-acting factors may be virally encoded proteins acting directly or through cooperation with cellular factors on the LTR sequences. Alternatively, HTLV infection might induce cellular factors that act to increase HTLV LTR function. The former explanation is preferred for two reasons. First, the trans-acting factors display type specificity. The factors present in HTLV-I infected cells act efficiently on Type I, but poorly on Type II LTR sequences, whereas the factors in Type II infected cells act to promote efficient transcription of both Type I and II LTR sequences. The ratio of CAT activity directed by plasmids that contain HTLV I and HTLV II LTR sequences is about 25:1 in HTLV I infected cells and only 3:1 in HTLV II infected cells. It is more likely that viral proteins rather than cellular factors would exhibit this type specificity. Second, the cellular program induced by HTLV I infection in HOS/M fibroblasts appears to differ substantially from that seen in HTLV infected lymphocytes. Nonetheless, the stimulation of HTLV I LTR promotion in HOS/M cells is as great as that seen in HTLV producer lymphocytes.

Both HTLV I and II contain sequences about 1,600 nucleotides long that are located between the 3' end of the envelope gene and the 5' end of the LTR (Seiki et al., 1983). DNA sequence analysis of this region of the HTLV I (Seiki et al., 1983) and HTLV II, reveals a highly conserved sequence about 1,000 nucleotides long that could encode a polypeptide about 330 amino acids long in both viruses. The level of CAT activity directed by the HTLVI LTR in the C81-66 cell line is comparable to the high activity in the HTLV infected cells.

Since this cell line produces no virus, yet contains a 42K dalton protein that is precipitable by anti-HTLV Serum (Essex, personal communication), it is tempting to speculate that this protein is the product of conserved open reading frame. The replication competent slowly transforming retroviruses, of other species that lack a corresponding long sequence at the 3' terminus. It has recently been found that CAT gene expression directed by the LTR elements of the Akv or SL3-3 murine leukemia viruses is not increased in cells infected by these viruses relative to uninfected cells. This difference between the HTLV viruses and the non-acute leukemia viruses is due to a product encoded at the 3' end of the HTLV genome.

Transacting transcriptional elements might alter the expression not only of viral genes, but also cellular genes. Transforming genes of certain DNA viruses, notably adenovirus, SV40 and herpes simplex virus have been reported to encode proteins that act to increase the rate of transcription of some genes in trans (Dennis, 1983; Nevins, 1981). Several observations suggest that this might be the case for HTLV infection. The IL2 receptor and another gene, HT3, are regularly expressed at high levels upon HTLV infection of T cells and in HTLV producing T cell lines. Transacting factors that alter the expression of the transfected transcriptional elements may also alter the expression of cellular genes and thus mediate the biological effects of HTLV infection.

Alteration of transcription of cellular genes by integrated non-acute leukemia viruses acting in cis has been reported (Hayward, 1981). Transacting transcriptional factors might account for several differences observed in the biology of HTLV from those of most other slowly transforming retroviruses.

No common site of HTLV integration has been found in cell lines derived from different patients or in primary tumors as has been found for several of the non-acute leukemia viruses. In this respect HTLV resembles bovine leukemia virus (another virus that contains a sequence of about 1,600 nucleotides located between the envelope and the LTR region) in which no consistent patterns of genomic integration have been observed (Kettman, 1982).

Chronic high levels of viremia are associated with disease induction for most of the non-acute leukemia viruses, whereas chronic viremia is absent in either HTLV or BLV induced disease.

Another difference between HTLV and other slowly transforming retroviruses is the ability of HTLV to immortalize primary lymphcytes in vitro. Viral transacting transcriptional factors could account for these three phenomena. No specific integration site would be required to induce cellular genes, nor would chronic infection be required to assure integration nearby cellular oncogenes. Immortalization as a consequence of viral infection might be expected to occur at a higher frequency as a result of viral induction of transcriptional factors than by integration of a defective provirus in the vicinity of a specific cellular oncogene.

The diseases associated with HTLV I, II and III differ in their clinical aggressiveness. These experiments demonstrate that the LTRs of these viral types differ with respect to their promotional strength, host cell range, and interactions with trans-acting transcriptional factors. The number and type of cells infected by the two viruses might differ as a consequence of the differing host range of the viral LTRs. Also, the level of expression of an immortalizing viral-encoded protein might differ in a critical target cell. Another possibility is that differential alteration of cellular transcriptional patterns by HTLV I, HTLV II, and HTLV III cis or trans-activating factors might have different phenotypic consequences. Although further research is clearly needed to elucidate the ultimate mechanisms whereby the transcriptional differences demonstrated herein might effect the clinical picture, the emerging role of the LTR as a disease determinant in animal leukemogenesis suggests that such an effort will provide insight into HTLV pathogenesis.

The present invention will be further illustrated by the following examples. The examples are provided to aid in the understanding of the invention and are not to be construed as a limitation on the scope of the claimed invention. All recombinant DNA techniques, including use of XhoI and Hind III synthetic DNA linker are according to standard procedures.

EXAMPLE 1

The recipient vector contains a Hind III-XhoI fragment of plasmid pSVIXCAT, a variant of plasmid pSV1CAT. PSV2CAT contains the SV4O early promoter enhancer region located 5' to the gene which codes for production of chloromphenol acetyl transferase (CAT). PSVIXCAT is identical to PSV2CAT except it lacks the 72 bp enhancer region. Digestion with Hind III-XhoI removes the SV40 promoter region, then allowing HTLV sequences to be placed 5' to CAT. The following plasmids were constructed: PV3R-I; a proviral clone containing the 3' LTR of HTLV I was cleaved with RSAl and ligated Hind III linker, DNA was then cleaved with Mbol, filled out with T4 polymerase and ligated to XhoI linkers. After Hind III-XhoI cleaving the 800 bp fragment was ligated to the CAT vector. PV3-II, and HTLV II proviral clone containing a 5' LTR was cleaved with EcoR1, filled in with T4 polymerase, ligated to Hind III linker, cleaved with Hind III-XhoI then the bp fragment was ligated to the CAT Vector. PV3-RII; an HTLV II proviral clone containing a 3' LTR was cleaved with BAMHI, filled out with T4 polymerase, and ligated to HIND III linkers. Digestion with HIND III-Xhoi produced a fragment that was ligated to the CAT vector. All constructions were confirmed by restriction enzyme mapping. Plasmid DNAs were purified by centrifugation in cessius chloride gradients.

EXAMPLE 2

NIH3T3 and CV-1 cells were transfected by a modification of the calcium phosphate coprecipitation technique (Graham, 1973). Approximately $1 \times 10^6$ cells were seeded on 10 cm$^2$ dishes 24 hours prior to addition of the Capo$_4$-DNA precipitate. One ml of the precipitate containing 4–10 ug of DNA was added to the medium, and the cells were incubated 4 hours at 37° C., then subjected to a 3 minute glycerol shock. CV-1 cells were subjected to a 10 minute DMSO shock 24 hours after transfection. All other cell lines were transfected by a modification of the DEAE dextran technique (Queen, 1983). Twenty-four hours before transfection adherent cells were seeded at a density of $10^6$ cells per 10 cm$^2$ dish. Immediately prior to transfection cells were typsinized, washed, and transfected in suspension with 5–8 ug of DNA an amount shown to be below saturation. Lymphocyte lines were transfected at a density of $1–5 \times 10^6$ cells per ml using 5–10 ug of DNA. Dot blot analysis confirmed comparable uptake between all cell lines. Cells were harvested 48 hours after transfection, and cellular extracts were prepared by freeze/thawing (three times). After a brief centrifugation to remove cell debris, extracts were analyzed for CAT activity as described by Gorman except that acetyl coenzyme A was present at 24 mm. Percent conversion of chloramphenicol to the acetylated forms was determined by ascending thin layer chromatography and liquid scintillation counting of the spots cut from the plate.

The HTLV LTR sequences of this invention are useful for the overproduction of proteins and like materials expressable by genes. In order to cause this overproduction, an HTLV LTR is first linked to the particular heterologous gene of interest in a configuration suitable for use of the HTLV LTR as a promoter region, and then that construct is employed in the transfection of a cell containing an HTLV genome which functions in a trans-acting manner. Thus, the concept requires a heterologous construction for the overproduction of expressable material.

A second embodiment for the overproduction of a protein or like product involves constructing a vector containing the luk sequence, the HTLV LTR sequence and the heterologous gene. This one vector is then rescued as an infectious virus particle. The heterologous gene must be configured so as to permit splicing and expression. The cell now "infected" with this material, is driven to super activity levels by luk and HTLV LTR, resulting in the overproduction of the heterologous gene product.

As employed herein, the generic term HTLV refers to all three viruses, type I, II and III. Regardless of which HTLV is employed, the heterologous gene product will be greatly stimulated in the presence of luk and the HTLV LTR.

Another utility envisioned for the HTLV LTR vectors of this invention makes use of the fact that when you hook the HTLV LTR onto a gene that is either linked to a cell or which expresses a surface protein, you permit recognition of that cell and consequent destruction thereof by the use of monoclonal or polyclonal antibodies. This is especially important in the treatment of HTLV mediated diseases, including AIDS.

Finally, it should be noted that the HTLV LTR vectors of the present invention may be employed in the production of vaccines. The first type of vaccine employs empty capsids (Mann, 1983) which can be produced by the deletion of a region which is non-essential for virion capsid production. These capsids can be employed to transfect a cell known to express virion proteins, such as for example HOS or HeLa. Here, the LTR would function, in the absence of the trans-acting factor (luk) to express virions at a low level. This low virion level induces immunity, yet doesn't induce the viral disease.

Vaccine production involves the infection of a cell which contains at a different chromosomal site, the luk gene, preengineered for expression, but not for expression of other viral proteins. A deletion in a pro-virus is first inserted into a cell containing twice the LTR's of HTLV, plus the luk region, but containing no other viral RNA. This construct then trans-activates a second virus transfected into the cell and thus produce a high rate of virality. Any of the HTLV LTR elements can be used in this construct. For example, if it is discovered that the HTLV III LTR is itself deleterious, the LTR for either HTLV I or HTLV II can be switched therefor.

In order to create a live attenuated vaccine, the functional part of the luk region is deleted, thus limiting the trans-activating ability of the virion. The virus is still capable of infecting cells, but is no longer capable of overproduction and therefore causing disease.

A further extension or utility for the HTLV LTR's of the present invention, on portions thereof (especially the tissue specific determinants) represents the first pharmaceutical use of these species. For example, the HTLV LTR's may be combined with an appropriate pharmaceutical carrier for delivery to a mammal of the tissue specific entity. Moreover, the tissue specific vectors may be employed in the delivery of antitumor like pharmaceutical agents, such as those described in the *Physicians' Desk Reference,* 38th ed., Medical Economics Co., Oraden, N.J. (1984), the disclosure of which is incorporated herein by reference.

The following references are provided as generally information. They are cited herein using the formate—(author, year). Each of these references is incorporated herein by reference.

1. B. J. Poiesz et al., *Proc. Natl. Acad, Sci, U.S.A.* 77, 7415 (1980); V. S. Kalyanaraman, M. Sarngadharan, P. Bunn, J. Minna, R. C. Gallo, *Nature* 294 271 (1981); M. Robert-Guroff, F. Ruscetti, L. Posner, B. Poiesz, R. C. Gallo, J. *Exp. Med.* 154, 1957 (1981); M. Yoshida, I. Miyoshi, Y. Hinuma, *Proc. Natl. Acad. Sci. U.S.A.* 79, 2031 (1982).

2. V. S. Kalyanaraman et al., *Science* 218, 571 (1982); I.S.Y. Chen, J. McLaughlin, J. C. Gasson, S. C. Clark, D. S. Golde, *Nature* 305, 502 (1983); E. P. Gelman, G. Franchini, V. Manzari, F. Wong-Staal, R. C. Gallo, *Proc. Natl. Acad. Sci. U.S.A.* 81, 993 (1984); G. M. Shaw et al., *Proc. Natl. Acad. Sci. U.S.A.*, in press; K. Shimotohno, D. W. Golde, M. Miwa, T. Sugimura, I.S.Y. Chen, *Proc. Natl. Acad. Sci. U.S.A.* 81, 1079 (1984); J. G. Sodroski et al., *Proc. Natl. Acad. Sci. U.S.A.*, in press; M. Seki, S. Hattori, M. Yoshida, *Proc. Natl. Acad. Sci. U.S.A.* 79, 6899 (1982).

3. M. Popovic et al., *Nature* 300, 63 (1982).

4. M. Popovic, M. G. Sarngadharan, E. Read, R. C. Gallo, *Science* 224, 297 (1984); R. C. Gallo et al., *Science* 224, 300 (1984); J. Schupbach et al., *Science* 224, 303 (1984); M. Sarngadharan, M. Popovic, L. Bruch, J. Schupbach, R. C. Gallo, *Science* 244, 306 (1984).

5. P. A. Chatis, C. A. Holland, J. W. Hartley, W. P. Rowe, N. Hopkins, *Proc. Natl. Acad. Sci. U.S.A.* 80, 4408 (1983); L. DesGroseillers, E. Rassart, P. Jolicoeur, *Proc. Natl. Acad. Sci. U.S.A.* 80, 4203 (1983); J. Lenz et al., *Nature* 308, 467 (1984).

6. H. M. Temin, *Cell* 27, 1(1981); H. M. Temin, *Cell* 28, 3 (1982).

7. C. M. Gorman, L. F. Moffat, B. H. Howard, *Mol. Cell Biol.* 2, 1044 (1982); C. M. Gorman, G. T. Merlino, M. C. Willingham, I. Pastan, B. Howard, *Proc. Natl. Acad. Sci. U.S.A.* 79, 6777 (1982).

8. F. L. Graham and A. J. van der Eb, *J. Virology* 52, 456 (1973); C. Queen and D. Baltimore, *Cell* 33, 729 (1983).

9. M. D. Walker, T. Edlund, A. M. Boulet, W. J. Rutter, *Nature* 306, 557 (1983).

10. G. J. Todaro and H. Green, *J. Cell Biol.* 17, 299 (1963).

11. F. C. Jensen et al, *Proc Natl. Acad. Sci. U.S.A.* 53, 53 (1964).

12. G. O. Gey. W. D. Coffman, M. T. Kubicek, *Cancer Res.* 12, 264 (1952).

13. B. Royer-Pokora, W. D. Peterson, W. A. Haseltine, *Exp. Cell Res.* 151, 408 (1984).

14. B. Howard, M. Estes, J. Pagano, *Biochem. Biophys. Acta* 228, 105 (1971); A. Loyter, G. A. Scangos, F. H. Ruddle, *Proc. Natl. Acad. Sci. U.S.A.* 79, 422 (1982).

14. P. J. Southern and P. Berg, *Mol. Appl. Gen.* 1, 227 (1982).

16. R. C. Gallo et al., *Proc. Natl. Acad. Sci. U.S.A.* 79, 5680 (1982).

17. N. Yamamoto, T. Matsumoto, Y. Koyanagi, Y. Tanaka, Y. Hinuma, *Nature* 299, 367 (1982); S. Z. Salahuddin and R. C. Gallo, personal communication.

18. A description and original literature references for this cell line are available in V. Mazari et al., *Proc. Natl. Acad. Sci. U.S.A.* 80 11 (1983).

19. I. Miyoshi et al., *Nature* 294, 770 (1981).

20. V. Manzari et al., *Proc. Natl. Acad. Sci. U.S.A.*, in press; B. Hahn et al., *Nature* 303, 253 (1983).

21. M. Popovic, G. Lange-Wantzin, P. S. Sarin, D. Mann, R. C. Gallo, *Proc. Natl. Acad. Sci. U.S.A.* 80, 5402 (1983).

22. P. Clapham, K. Nagy, R. Chengsong-Popov, M. Exley, R. W. Weiss, *Science* 222, 1125 (1983).

23. B. Hahn et al., *Nature* 305, 340 (1983).

24. R. C. Gallo and F. Wong-Staal, *Blood* 60, 545 (1982).

25. N. Yamamoto, M. Okada, Y. Koyanagi, M. Kannagi, Y. Hinuma, *Science* 217, 737 (1982).

26. M. Seiki, S. Hattori, Y. Hirayama, M. Yoshida, *Proc. Natl. Acad. Sci. U.S.A.* 80, 3618 (1983).

27. J. Brady, J. B. Bolen, M. Radonovich, N. Salzman, G. Khoury, *Proc. Natl. Acad. Sci. U.S.A.* 81, 2040 (1984).

28. N. Jones and T. Shenk, *Proc. Natl. Acad. Sci. U.S.A.* 76, 3665 (1979); J. R. Nevins, *Cell* 26 213 (1981); A. Berk. F. Lee, T. Harrison, J. Williams, R. A. Sharp, *Cell* 17, 935 (1979); R. B. Gaynor, D. Hillman, A. Berk, *Proc. Natl. Acad. Sci. U.S.A.* 81, 1193 (1984).

29. V. Manzari et al, *Proc. Natl. Acad. Sci. U.S.A.* 80 1574 (1983).

30. W. S. Hayward, B. G. Neel, S. M. Astrin, *Nature (London)* 290 475 (1981).

31. R. Mann, R. C. Mulligan, D. Baltimore, *Cell,* 33 153 (1983).

32. H. Mitsuya, H-G. Guo, M. Megson, C. Trainor, M. S. Reitz, Jr., S. Broder, *Science,* 223 1293 (1984).

33. U.S. patent application Ser. No. 614,274 Filed 25 May 1984, inventors Hazeltine, Lenz, Rosen and Celander, entitled "LTR Vectors, Methods Of Preparation and Use".

What is claimed is:

1. A vector comprising a DNA sequence coding for a desired gene product, a DNA sequence coding for an HTLV-I or -II trans-acting factor and a portion of an HTLV-I or -II LTR responsive to the HTLV trans-acting factor.

2. The vector of claim 1, wherein the DNA coding for the trans-acting factor comprises and HTLV luk gene.

3. The vector of claim 2, wherein the responsive portion of the HTLV LTR is the U3 region and a portion of the R Region of HTLV LTR.

4. The vector of claim 3 further comprising an enhancer located 5' to the gene to be expressed.

5. The vector of claim 2, wherein the HTLV LTR is the HTLV-I LTR.

6. The vector of claim 2 wherein the HTLV LTR is the HTLV-II LTR.

7. A gene expression system comprising an expression vector and a DNA segment coding for an HTLV-I or -II trans-acting factor, wherein the expression vector comprises a preselected gene coding for a desired product, which is under the control of an HTLV-I or -II regulatory element responsive to the trans-acting factor and wherein the expression vector codes for a product other than a complete HLTV virus.

8. The gene expression system of claim 7, wherein the preselected gene is heterologous to both the trans-acting factor and the regulatory element.

9. The gene expression system of claim 8, wherein the trans-acting factor encoding DNA segment comprises an HTLV luk gene.

10. The gene expression system of claim 8, wherein the trans-acting factor encoding DNA segment comprises an HTLV-I luk gene.

11. The gene expression system of claim 8, wherein the expression vector codes for expression of a viral surface glycoprotein.

12. The gene expression system of claim 7, wherein the HTLV regulatory element comprises the U3 region and a portion of the R region of the HTLV LTR.

13. The gene expression system of claim 7, wherein the HTLV regulatory element comprises the HTLV-I LTR.

14. The gene expression system of claim 7, wherein the HTLV regulatory element comprises the HTLV-II LTR.

15. A method for stimulating the production of a gene product, which comprises:
    (a) inserting an expressible DNA segment coding for a trans-acting factor into a host cell, the trans-acting DNA segment comprising a segment derived from the genome of an HTLV-I or -II virus, which segment codes for a trans-acting factor;
    (b) inserting an expression vector into the host cell, the expression vector comprising the gene which codes for the gene product to be expressed and an HTLV-I or -II regulatory element which is responsive to the trans-acting factor produced by the trans-acting DNA segment; and
    (c) cultivating the host cell.

16. The method of claim 15, wherein the gene to be expressed is heterologous to both the trans-acting factor and the regulatory element.

17. The method of claim 15, wherein the trans-acting DNA segment comprises an HTLV-I luk gene.

18. The method of claim 15, wherein the trans-acting DNA segment comprises an HTLV-II luk gene.

19. The method of claim 15, wherein the expression vector codes for expression of a viral surface glycoprotein.

20. The method of claim 15, wherein the regulatory element comprises an HTLV LTR.

21. The method of claim 20, wherein the HTLV LTR is an HTLV-I LTR.

22. The method of claim 20, wherein the HTLV LTR is HTLV-II LTR.

23. The method of claim 15, wherein the level of production of the gene product in the presence of the trans-acting factor is at least five times greater than the level in the absence of the trans-acting factor.

24. The method of claim 15, wherein the host cell is a fibroblast cell, a lymphoid cell, an epithelial cell, or a hamster ovary cell.

25. The method of claim 24, wherein the host cell is of human, murine, feline or simian origin.

26. The method of claim 25, wherein the host cell is a fibroblast, lymphocyte or epithelial cell.

* * * * *